United States Patent
Wampler et al.

(10) Patent No.: US 7,416,525 B2
(45) Date of Patent: Aug. 26, 2008

(54) ROTARY BLOOD PUMP

(75) Inventors: Richard K. Wampler, Loomis, CA (US); David M. Lancisi, Folsom, CA (US)

(73) Assignee: Myrakelle, LLC, Loomis, CA (US)

(*) Notice: Subject to any disclaimer, the term of this patent is extended or adjusted under 35 U.S.C. 154(b) by 506 days.

(21) Appl. No.: 10/937,091

(22) Filed: Sep. 9, 2004

(65) Prior Publication Data

US 2005/0084399 A1    Apr. 21, 2005

Related U.S. Application Data

(60) Provisional application No. 60/504,233, filed on Sep. 18, 2003.

(51) Int. Cl.
*A61M 1/10* (2006.01)
(52) U.S. Cl. ....................................................... 600/16
(58) Field of Classification Search ............... 417/423.7, 417/423.1, 356, 900; 604/131, 151; 600/16, 600/17
See application file for complete search history.

(56) References Cited

U.S. PATENT DOCUMENTS

| | | | |
|---|---|---|---|
| 4,779,614 A | 10/1988 | Moise | |
| 4,806,080 A | 2/1989 | Mizobuchi et al. | |
| 5,049,134 A | 9/1991 | Golding et al. | |
| 5,055,005 A | 10/1991 | Kletschka | |
| 5,112,200 A | 5/1992 | Isaacson et al. | |
| 5,195,877 A | 3/1993 | Kletschka | |
| 5,209,650 A | 5/1993 | Lemieux | |
| 5,211,546 A | 5/1993 | Isaacson et al. | |
| 5,324,177 A | 6/1994 | Golding et al. | |
| 5,360,445 A | 11/1994 | Goldowsky | |
| 5,370,509 A | 12/1994 | Golding et al. | |
| 5,385,581 A | 1/1995 | Bramm et al. | |
| 5,470,208 A | 11/1995 | Kletschka | |
| 5,685,700 A | 11/1997 | Izraelev | |
| 5,695,471 A | 12/1997 | Wampler | |

(Continued)

FOREIGN PATENT DOCUMENTS

EP          810374 A2          12/1997

(Continued)

OTHER PUBLICATIONS

G. H. Jang, et al., "Nonlinear Dynamic Analysis of a Hydrodynamic Journal Bearing Considering the Effect of a Rotating or Stationary Herringbone Groove", ASME Journal of Tribology, STLE/ASME Tribology Conference, San Francisco, California Oct. 22-24, 2001, pp. 297-304.

(Continued)

*Primary Examiner*—Carl H. Layno
*Assistant Examiner*—Frances P Oropeza
(74) *Attorney, Agent, or Firm*—Inskeep IP Group, Inc.

(57) ABSTRACT

Various "contactless" bearing mechanisms including hydrodynamic, hydrostatic, and magnetic bearings are provided for a rotary pump as alternatives to mechanical contact bearings. These design features may be combined. In one embodiment, the pump apparatus includes a rotor having a bore, a ring-shaped upper rotor bearing magnet, and a ring-shaped lower rotor bearing magnet. The bearing magnets are concentric with the bore. The lack of mechanical contact bearings enables longer life pump operation and less damage to working fluids such as blood.

10 Claims, 12 Drawing Sheets

U.S. PATENT DOCUMENTS

| | | |
|---|---|---|
| 5,713,730 A | 2/1998 | Nosé et al. |
| 5,746,575 A | 5/1998 | Westphal et al. |
| 5,840,070 A | 11/1998 | Wampler |
| 5,890,883 A | 4/1999 | Golding |
| 5,938,412 A | 8/1999 | Izraelev |
| 5,947,703 A | 9/1999 | Nojiri et al. |
| 6,071,093 A | 6/2000 | Hart |
| 6,080,133 A | 6/2000 | Wampler |
| 6,155,969 A | 12/2000 | Schima et al. |
| 6,176,848 B1 | 1/2001 | Rau et al. |
| 6,227,797 B1 | 5/2001 | Watterson et al. |
| 6,227,817 B1 | 5/2001 | Paden |
| 6,227,820 B1 | 5/2001 | Jarvik |
| 6,234,772 B1 | 5/2001 | Wampler |
| 6,234,998 B1 | 5/2001 | Wampler |
| 6,244,835 B1 | 6/2001 | Antaki et al. |
| 6,247,892 B1 | 6/2001 | Kazatchkov et al. |
| 6,250,880 B1 | 6/2001 | Woodard et al. |
| 6,264,635 B1 | 7/2001 | Wampler et al. |
| 6,293,901 B1 | 9/2001 | Prem |
| 6,368,083 B1 * | 4/2002 | Wampler .............. 417/423.7 |
| 6,394,769 B1 | 5/2002 | Bearnson et al. |
| 6,447,266 B2 | 9/2002 | Antaki et al. |
| 6,537,315 B2 * | 3/2003 | Yamazaki et al. .......... 623/3.13 |
| 6,595,762 B2 | 7/2003 | Khanwilkar et al. |
| 6,609,883 B2 | 8/2003 | Woodard et al. |
| 6,638,011 B2 | 10/2003 | Woodard et al. |
| 6,688,861 B2 | 2/2004 | Wampler |
| 2001/0031210 A1 | 10/2001 | Antaki et al. |

FOREIGN PATENT DOCUMENTS

| | | |
|---|---|---|
| EP | 1481699 A | 12/2004 |
| WO | WO 94/09274 | 4/1994 |
| WO | WO 95/00185 | 1/1995 |
| WO | WO 97/37698 | 10/1997 |
| WO | WO 98/41759 | 9/1998 |
| WO | WO 98/46879 | 10/1998 |
| WO | WO 99/01663 | 1/1999 |
| WO | WO 99/12587 | 3/1999 |
| WO | WO 99/53974 | 10/1999 |

OTHER PUBLICATIONS

G. H. Jang, et al., "Stability Analysis of a Hydrodynamic Journal Bearing with Rotating Herringbone Grooves", ASME Journal of Tribology, ASME/STLE Tribology Conference, Cancun, Mexico Oct. 27-30, 2002, pp. 291-300.

Fluid Dynamic Bearings (FDB): New Technology to Replace Ball Bearings in Western Digital Hard Drives, Western Digital, Jul. 2002.

* cited by examiner

ROTARY BLOOD PUMP

CROSS-REFERENCE TO RELATED APPLICATIONS

This application claims the benefit of U.S. Provisional Application No. 60/504,233 of Wampler, et al. filed Sep. 18, 2003.

FIELD OF THE INVENTION

This invention relates to the field of rotary pumps. In particular, this invention is drawn to bearings for various rotor and impeller architectures.

BACKGROUND OF THE INVENTION

Typical rotary pumps utilize an impeller wherein the movement of the impeller is constrained in five degrees of freedom (two angular, three translational) by mechanical contact bearings. Some working fluids may be damaged by the mechanical contact bearings. Blood pumped through pumps with contact bearings can experience hemolysis, i.e., damage to blood cells. In general, a hydraulically efficient and power efficient pump that can handle delicate working fluids such as blood is desirable for some applications.

U.S. Pat. No. 6,234,772 B1 of Wampler, et al., ("Wampler") describes a centrifugal blood pump having a repulsive radial magnetic bearing and an axial hydrodynamic bearing. U.S. Pat. No. 6,250,880 B1 of Woodard, et al. ("Woodard") describes a centrifugal blood pump with an impeller supported exclusively by hydrodynamic forces.

Both blood pumps are based on an axial flux gap motor design. The pump impeller carries the motor drive magnets thus serving as a motor rotor. In both cases, the drive magnets are disposed within the blades of the impeller. Drive windings reside outside the pump chamber but within the pump housing that serves as the motor stator. Integration of the motor and pump enables the elimination of drive shafts and seals for the pumps. The pump/motors include a back iron to increase the magnetic flux for driving the impeller.

Both blood pumps suffer from hydraulic inefficiencies due at least in part to the large, unconventional blade geometry required for disposing the magnets within the impeller blades.

The natural attraction between the magnets carried by the impeller and the back iron creates significant axial forces that must be overcome in order for the pump to work efficiently. Hydrodynamic bearings can damage blood cells as a result of shear forces related to the load carried by the hydrodynamic bearings despite the lack of contact between the impeller and the pump housing. Thus exclusive reliance on hydrodynamic bearings may be harmful to the blood.

SUMMARY OF THE INVENTION

In view of limitations of known systems and methods, various "contactless" bearing mechanisms are provided for a rotary pump as alternatives to mechanical contact bearings. Various rotor and housing design features are provided to achieve hydrodynamic, hydrostatic, or magnetic bearings. These design features may be combined. The lack of mechanical contact bearings enables longer life pump operation and less damage to working fluids such as blood.

In one embodiment, a pump includes a pump housing defining a pumping chamber. The pump housing has a spindle extending into the pumping chamber. The spindle further comprises an upper spindle magnet and a lower spindle magnet. A rotor configured to rotate about the spindle has an upper rotor magnet and a lower rotor magnet. The upper spindle and rotor magnets are arranged to repel each other. The lower spindle and rotor magnets are arranged to repel each other.

In one embodiment, the pump includes a hydrostatic thrust bearing. The pump housing has a spindle extending from a wall of the pump housing into the pumping chamber defined by the pump housing. The spindle has a stepped portion adjacent the wall. In one embodiment, the stepped portion is defined by a change in spindle diameter.

In various embodiments, the rotor includes either paddles or grooves disposed about the periphery of the rotor. The rotor may include a grooved bore. The grooved bore may be combined with the grooved or paddled periphery. The paddles and grooves generate a hydrostatic thrust forces during rotation of the rotor.

The pump may include both the hydrostatic and magnetic thrust bearings. In addition, the pump may incorporate a hydrodynamic thrust or a hydrodynamic radial bearing, or both.

BRIEF DESCRIPTION OF THE DRAWINGS

The present invention is illustrated by way of example and not limitation in the figures of the accompanying drawings, in which like references indicate similar elements and in which.

DETAILED DESCRIPTION

Figure 1:
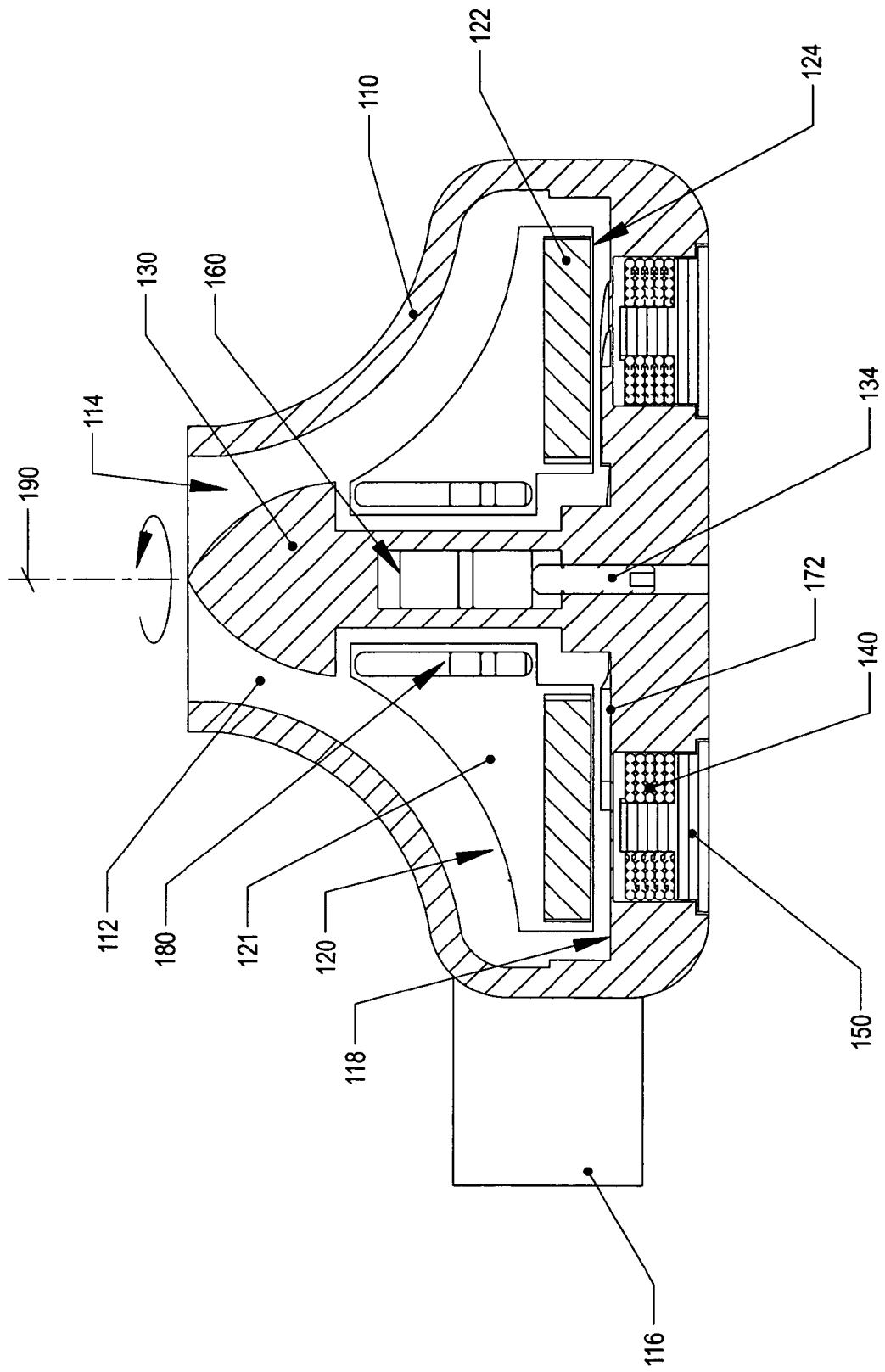
FIG. 1 illustrates a cross-section of a pump having a passive magnetic axial bearing.

FIG. 1 illustrates one embodiment of a centrifugal blood pump. The pump comprises a housing 110 defining a pumping chamber 112 between an inlet 114 and an outlet 116. Within the pumping chamber, a rotor 120 rotates about a spindle 130 protruding from a base of the pump housing. The rotor further comprises a bladed portion defining an impeller that provides the fluid moving surfaces. The impeller comprises one or more blades 121 that move fluids when the impeller rotates.

The terms "rotor" and "impeller" may be used interchangeably in some contexts. For example, when the rotor is rotating, the blade portion of the rotor is inherently rotating such that reference to rotation of either the impeller or the rotor is sufficient to describe both. When necessary, however, the term "non-bladed portion of the rotor" or "rotor excluding the impeller" may be used to specifically identify portions of the rotor other than the blades. Each blade of the rotor may separately be referred to as an impeller, however the term "impeller" is generally used to refer to a collective set of one or more blades.

The pump is based upon a moving magnet axial flux gap motor architecture. In one embodiment, the motor is a brushless DC motor. Drive magnets 122 carried by the rotor have magnetic vectors parallel to the rotor axis of rotation 190. In the illustrated embodiment, the drive magnets are disposed within a non-bladed portion of the rotor.

Drive windings 140 are located within the pump housing. Power is applied to the drive windings to generate the appropriate time-varying currents that interact with the drive magnets in order to cause the impeller to rotate. A back iron 150 enhances the magnetic flux produced by the motor rotor magnets. In one embodiment, either the face 124 of the bottom of the rotor or the opposing face 118 provided by the lower pump housing have surfaces (e.g., 172) contoured to produce a hydrodynamic bearing when the clearance between the rotor and the housing falls below a pre-determined threshold. In one embodiment, the pre-determined threshold is within a range of 0.0002 inches to 0.003 inches.

The natural attraction between the back iron 150 and the drive magnets 122 carried by the rotor can create a significant axial load on the rotor. This axial load is present in centrifugal pumps based on an axial flux gap motor architecture such as Wampler or Woodard. Woodard and Wampler both rely on hydrodynamic thrust bearings to overcome this axial loading force. Despite the lack of contact, hydrodynamic bearings can still damage blood cells as a result of shear forces related to the load carried by the hydrodynamic bearings.

The repulsive radial magnetic bearing of Wampler exacerbates the axial loads created by the magnetic attraction between the drive magnets and the back iron. Although the repulsive radial magnetic bearing creates radial stability, it introduces considerable axial instability. This axial instability can contribute further to the axial loading. This additional axial loading creates greater shear forces for any axial hydrodynamic bearing that can cause undesirable hemolysis for blood applications. In addition, the power required to sustain the hydrodynamic bearing increases as the load increases. Thus highly loaded hydrodynamic bearings can impose a significant power penalty.

The blood pump of FIG. 1 includes a magnetic axial bearing that serves to reduce or offset the axial load imposed on the rotor by the interaction between the drive magnets and the back iron. The axial magnetic bearing is formed by the interaction between a spindle magnet assembly 160 disposed within the spindle and a rotor magnet assembly 180 carried by the rotor. In the illustrated embodiment, the rotor magnet assembly 180 is disposed proximate the impeller, but the magnets of the rotor magnet assembly are not located within the blades. A set screw 134 permits longitudinal adjustment of the axial position of the axial magnetic bearing by moving the spindle magnet assembly along a longitudinal axis of the spindle.

Figure 2:
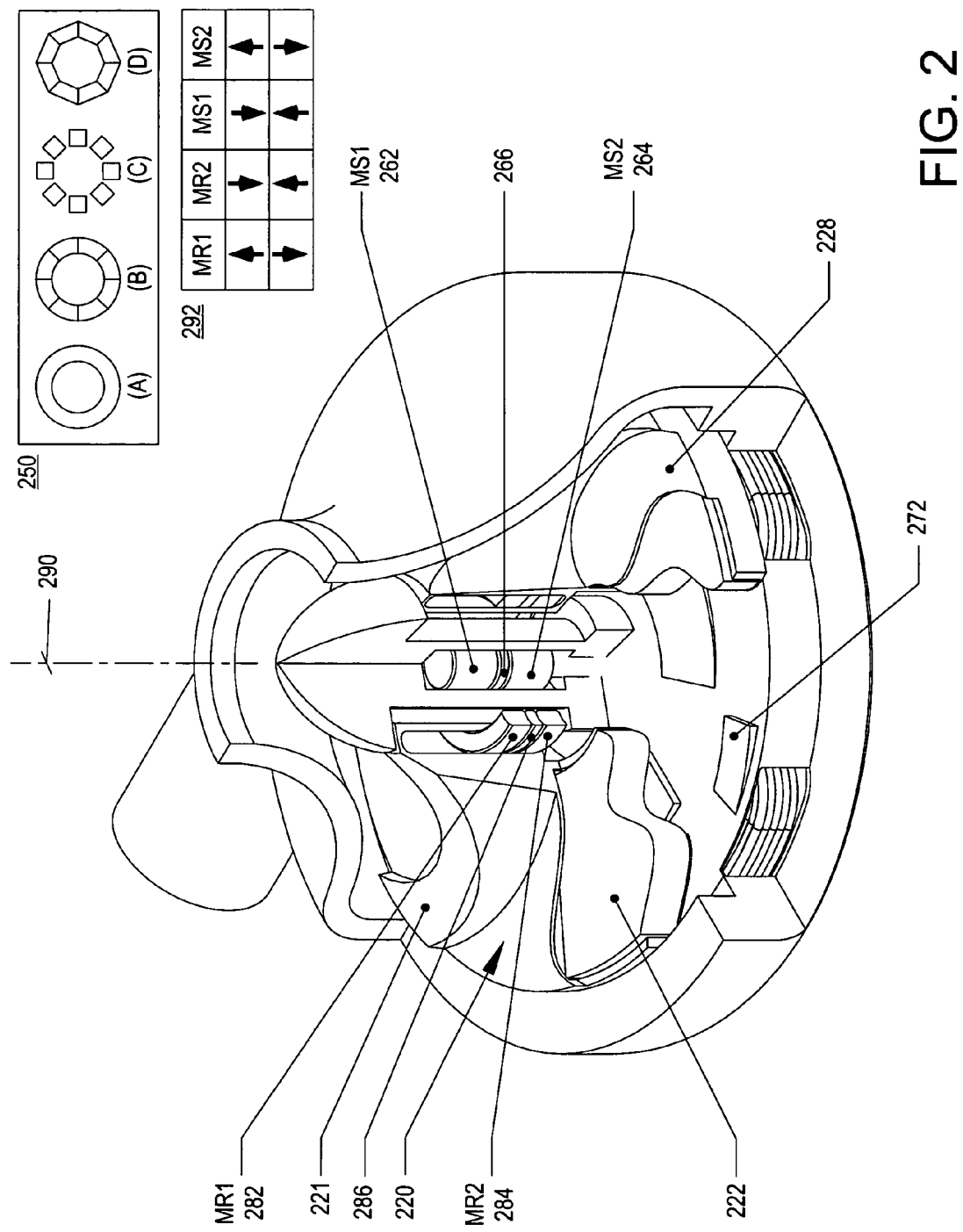
FIG. 2 illustrates one embodiment of the passive magnetic axial bearing.

FIG. 2 illustrates one embodiment of the axial magnetic bearing. The rotor magnet assembly includes a first rotor bearing magnet 282 and a second rotor bearing magnet 284 proximately disposed to each other. The first and second rotor bearing magnets are permanent magnets. In one embodiment, a pole piece 286 is disposed between them. A pole piece or flux concentrator serves to concentrate the magnetic flux produced by rotor bearing magnets 282 and 284. In an alternative embodiment, element 286 is merely a spacer to aid in positioning the first and second bearing magnets 282, 284 and does not serve to concentrate any magnetic flux. In other embodiments, element 286 is omitted so that the rotor magnet assembly does not include a spacer or a pole piece element.

In one embodiment, elements 282 and 284 are monolithic, ring-shaped permanent magnets (see, e.g., 250 (a)). In alternative embodiments, the bearing magnets may be non-monolithic compositions (see, e.g.,. 250 (b), (c), (d)). For example, a bearing magnet may be composed of a plurality of pie-shaped, or arcuate segment-shaped (250 (b)), or other shapes (250 (c), (d)) of permanent magnet elements that collectively form a ring-shaped permanent magnet structure.

The rotor axial bearing magnet assembly is distinct from the drive magnets 222 carried by a portion of the rotor other than the blades 221. In the illustrated embodiment, the drive magnets are disposed within the non-bladed portion 228 of the rotor.

The spindle magnet assembly includes a first spindle bearing magnet 262 and a second spindle bearing magnet 264. The first and second spindle bearing magnets are permanent magnets. In one embodiment, a pole piece 266 is disposed between them. Pole piece 266 concentrates the magnetic flux produced by the spindle bearing magnets 262 and 264. In an alternative embodiment, element 266 is merely a spacer for positioning the first and second spindle bearing magnets and does not serve to concentrate any magnetic flux. In other embodiments, element 266 is omitted so that the spindle magnet assembly does not include a spacer or a pole piece element.

In the illustrated embodiment, permanent magnets 262 and 264 are cylindrical. Other shapes may be utilized in alternative embodiments. The ring-shaped rotor magnets rotate with the impeller about a longitudinal axis of the spindle that is shared by the spindle bearing magnet assembly.

The permanent magnets of each of the spindle and rotor bearing assemblies are arranged such that the magnetic vectors of the individual magnets on either side of the intervening pole pieces oppose each other. Each side of a given pole piece is adjacent the same pole of different magnets. Thus the magnetic vectors of magnets 262 and 264 oppose each other (e.g., N-to-N or S-to-S). Similarly, the magnetic vectors of magnets 282 and 284 oppose each other.

The orientation of the magnets is chosen to establish an axial attraction whenever the bearings are axially misaligned. Note that the relative orientations of the spindle and rotor magnet assemblies are selected so that the spindle and rotor magnet assemblies attract each other (e.g., S-to-N, N-to-S). The magnet vector orientation selected for the magnets of one assembly determines the magnetic vector orientation for the magnets of the other assembly. Table 292 illustrates the acceptable magnetic vector combinations for the first and second rotor bearing magnets (MR1, MR2) and the first and second spindle bearing magnets (MS1, MS2). Forces such as the magnetic attraction between the back iron and drive magnets that tend to axially displace the magnet bearing assemblies are offset at least in part by the magnetic attraction between the axial bearings that provide an axial force to restore the axial position of the rotor.

FIG. 2 also illustrates wedges or tapered surfaces 272 that form a portion of a hydrodynamic bearing when the clearance between a face of the non-bladed portion of the rotor (see, e.g., bottom face 124 of FIG. 1) and the back of the pump housing falls below a pre-determined threshold. In various embodiments, this pre-determined threshold is within a range of 0.0002 inches to 0.003 inches. Thus in one embodiment, the pump includes an axial hydrodynamic bearing. The surface geometry providing the axial hydrodynamic bearing may be located on the rotor or the housing.

Although the spindle magnet assembly is intended to provide an axial magnetic bearing, the attractive force between the spindle and rotor magnet assemblies also has a radial component. This radial component may be utilized to offset radial loading of the impeller due to the pressure gradient across the impeller. The radial component also serves as a pre-load during initial rotation and a bias during normal operation to prevent eccentric rotation of the rotor about the spindle. Such an eccentric rotation can result in fluid whirl or whip which is detrimental to the pumping action. The biasing radial component helps to maintain or restore the radial position of the rotor and the pumping action, for example, when the pump is subjected to external forces as a result of movement or impact.

Instead of a spindle magnet assembly interacting with a rotor bearing magnet assembly to form the magnetic bearing, a ferromagnetic material might be used in lieu of one of a) the spindle magnet assembly, or b) the rotor bearing magnet assembly (but not both) in alternative embodiments.

The alternative magnetic bearing is still composed of a spindle portion and a rotor portion, however, one of the spindle and the rotor portions utilizes ferromagnetic material while the other portion utilizes permanent magnets. The ferromagnetic material interacts with the magnets to create a magnetic attraction between the rotor and spindle. Examples of ferromagnetic materials includes iron, nickel, and cobalt.

In one embodiment, the ferromagnetic material is "soft iron". Soft iron is characterized in part by a very low coercivity. Thus irrespective of its remanence or retentivity, soft iron is readily magnetized (or re-magnetized) in the presence of an external magnetic field such as those provided by the permanent magnets of the magnetic bearing system.

Figure 3:
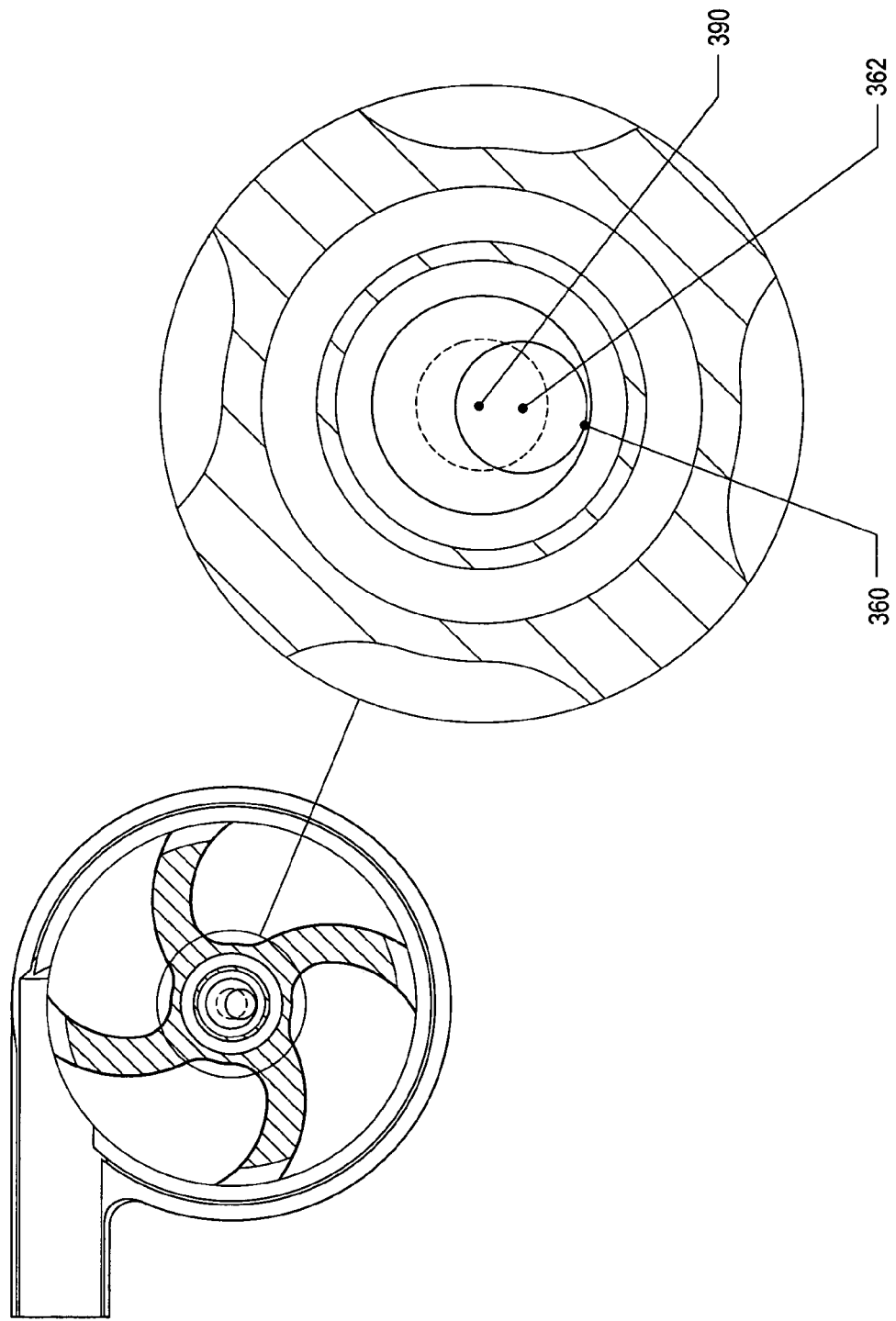
FIG. 3 illustrates center and off-center placement of the passive magnetic axial bearing.

FIG. 3 illustrates various locations for the placement of the spindle portion of the magnetic bearing. In one embodiment, the spindle magnet assembly 360 is axially aligned with a longitudinal axis 390 of the spindle so that the spindle and spindle magnet assembly share the same central longitudinal axis. In an alternative embodiment, the spindle magnet assembly is radially offset so that the spindle and spindle magnet assembly do not share the same central axis. In particular, the longitudinal axis 362 of the spindle magnet assembly 360 is displaced from the longitudinal axis 390 of the spindle. This latter positioning may be desirable to provide some radial biasing force. A difference in pressure across the impeller tends to push the impeller radially towards one side of the pump housing. This radial load may be offset at least in part by offsetting the spindle magnet assembly.

Although the spindle and rotor magnet assemblies are illustrated as comprising 2 magnetic elements each, the magnet assemblies may each comprise a single magnet instead. A greater spring rate may be achieved with multiple magnetic elements per assembly configured as illustrated instead of a single magnet per assembly. The use of two magnetic elements per assembly results in a bearing that tends to correct bi-directional axial displacements from a position of stability (i.e., displacements above and below the point of stability) with a greater spring rate than single magnetic elements per assembly.

Figure 4:
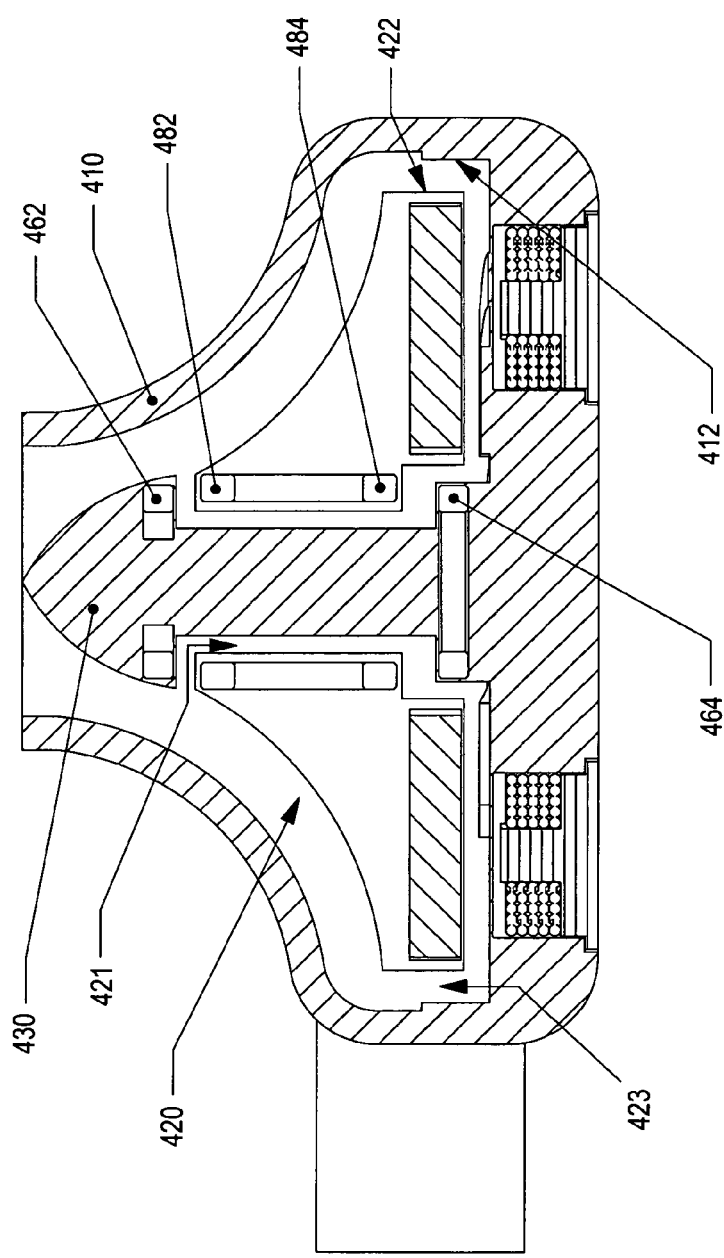
FIG. 4 illustrates one embodiment of a passive magnetic repulsive axial bearing.

FIG. 4 illustrates an alternative axial magnetic bearing. The axial magnetic bearing is based upon axially repulsive magnetic forces generated between the rotor 420 and the spindle 430. The axial magnetic bearing is formed from opposing upper magnets in the rotor and spindle and opposing lower magnets in the rotor and spindle.

In the illustrated embodiment, the rotor includes one or more upper bearing magnetic elements 482 and one or more lower bearing magnetic elements 484. The spindle includes one or more upper bearing magnetic elements 462 and one or more lower bearing magnetic elements 464. The spindle and rotor upper bearing magnet elements (462, 482) are positioned so that their respective magnetic vectors oppose each other as illustrated. Similarly, the spindle and rotor lower bearing magnet elements (464, 484) are positioned so that their respective magnetic vectors oppose each other as illustrated.

Figure 5:
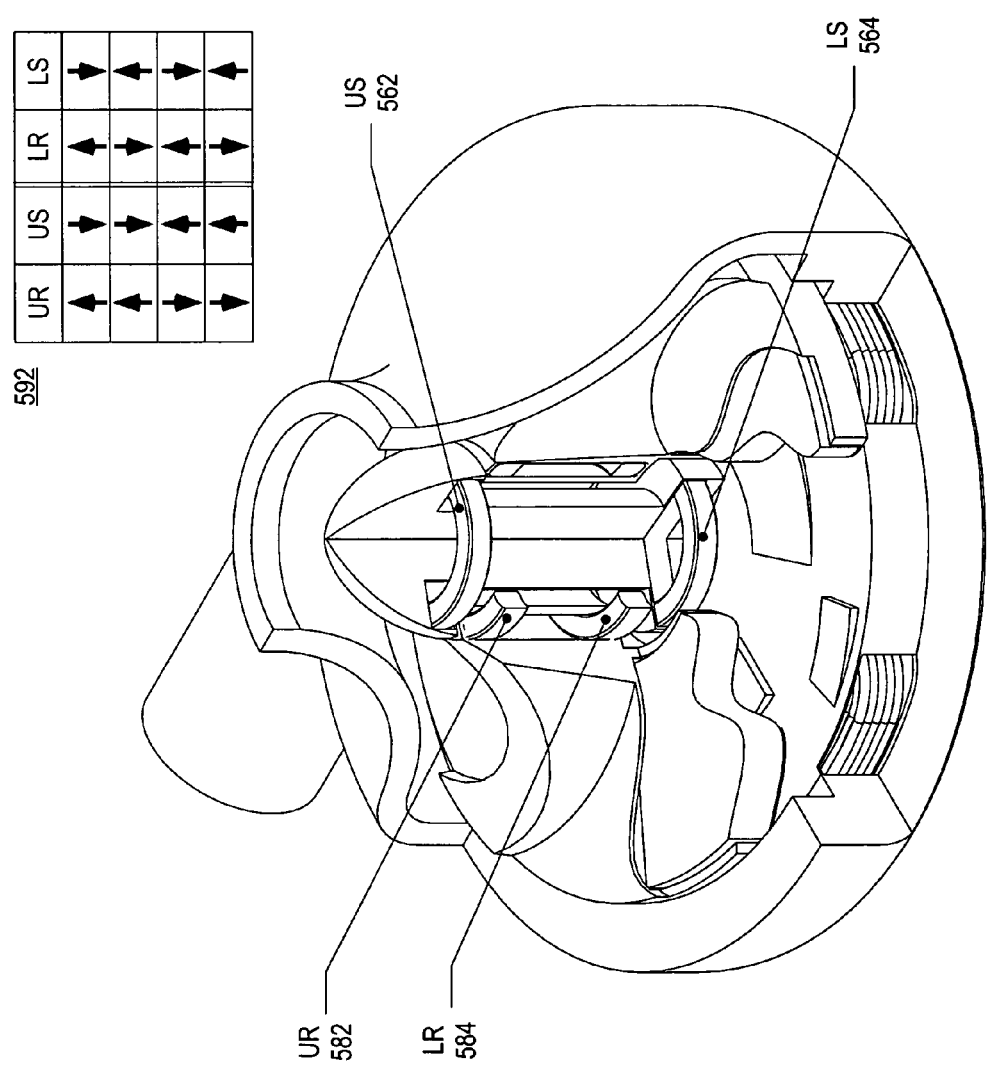
FIG. 5 illustrates one embodiment of a passive magnetic repulsive axial bearing.

FIG. 5 illustrates one embodiment of the upper and lower magnetic elements forming the upper and lower magnetic bearings in the spindle and rotor. The rotor upper 582 and lower 584 magnetic elements are ring-shaped. The upper and lower rings may each be formed from a single magnet or a plurality of distinct magnetic elements. The opposing spindle upper 562 and lower 564 magnetic elements are similarly ring-shaped.

The magnetic vectors of the upper rotor and upper spindle bearing magnets oppose each other. Similarly, the magnetic vectors of the lower rotor and lower spindle bearing magnets oppose each other. Given that there is no magnetic coupling between the upper and lower spindle magnet elements the relative magnetic vector orientation between the upper and lower spindle magnetic elements is irrelevant. Similarly, the relative magnetic vector orientation between the upper and lower rotor magnetic elements is irrelevant. Table 592 sets forth a number of combinations for the magnetic vectors of the upper rotor (UR), upper spindle (US), lower rotor (LR), and lower spindle (LS) magnetic elements.

The magnetic force generated by the axial magnetic bearing will exhibit a radial component in addition to their axial components. The radial component will tend to de-stabilize the rotor. In particular, the radial component may introduce radial position instability for the magnetic bearings of either FIG. 1 or 4.

This radial instability may be overcome using radial hydrodynamic bearings. Referring to FIG. 4, the pump may be designed for a radial hydrodynamic bearing (i.e., hydrodynamic journal bearing) located between the spindle 430 and the rotor along the bore of the rotor. Alternatively, the pump may be designed for a radial hydrodynamic bearing located between the periphery 422 of the rotor and the wall 412 of the lower portion of housing 410. In one embodiment, the pump includes both a radial hydrodynamic bearing (i.e., hydrodynamic journal bearing) in both locations.

The clearances illustrated in FIG. 4 are exaggerated. Hydrodynamic journal bearings require narrow clearances to be effective. In various embodiments, the hydrodynamic journal bearing clearances range from 0.0005-0.020 inches. Although the pump of FIG. 4 has been provided as an example, the radial hydrodynamic bearing(s) may similarly be incorporated into the pump of FIG. 1. The surface geometries suitable for axial (thrust) or radial (journal) hydrodynamic bearings may be located on either the rotor or on an associated portion of the housing (or spindle). In one embodiment, the surface geometry includes features such as one or more pads (i.e., a feature creating an abrupt change in clearance such as a step of uniform height). In alternative embodiments, the surface geometry includes features such as one or more tapers.

Figure 6:
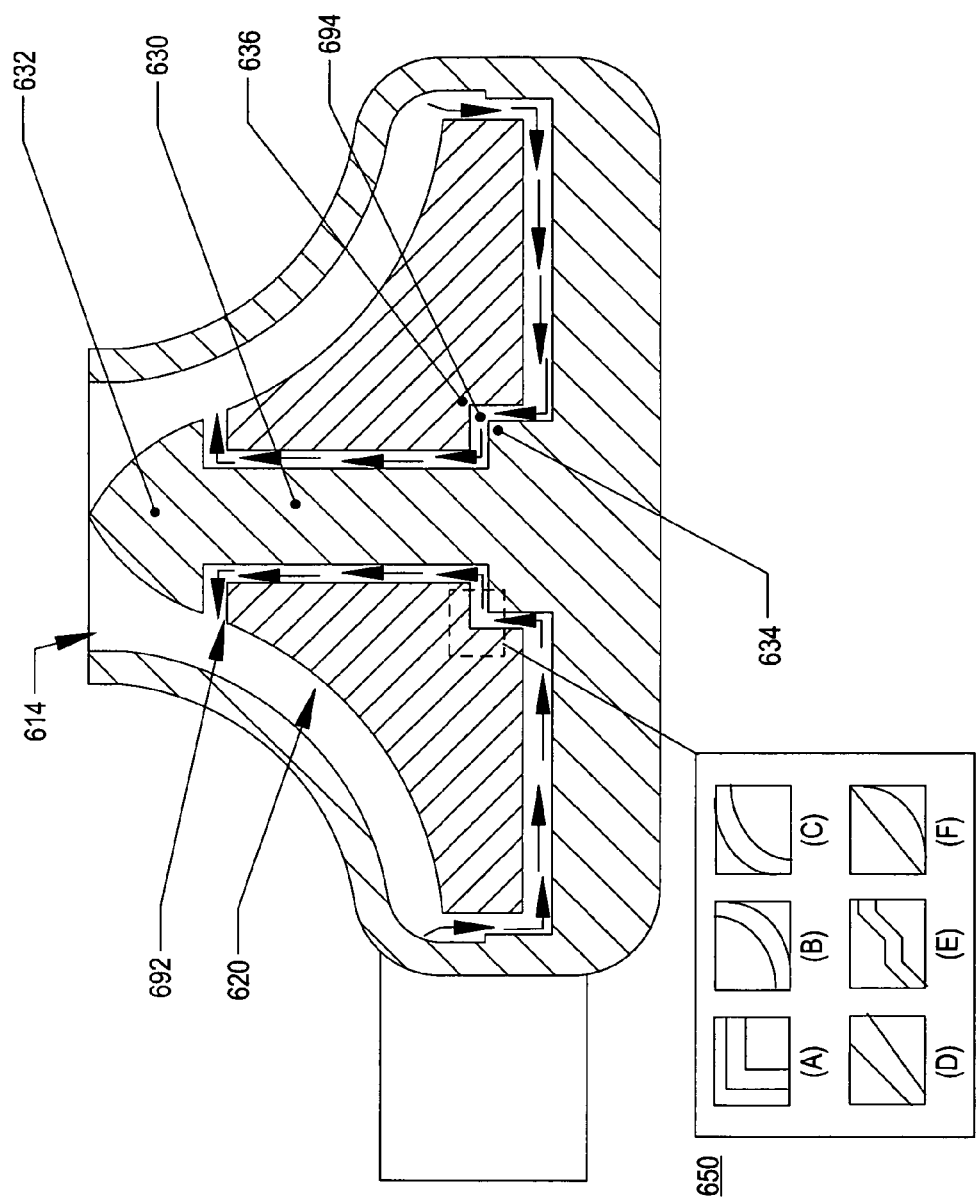
FIG. 6 illustrates an axial hydrostatic bearing in a first position.
Figure 7:
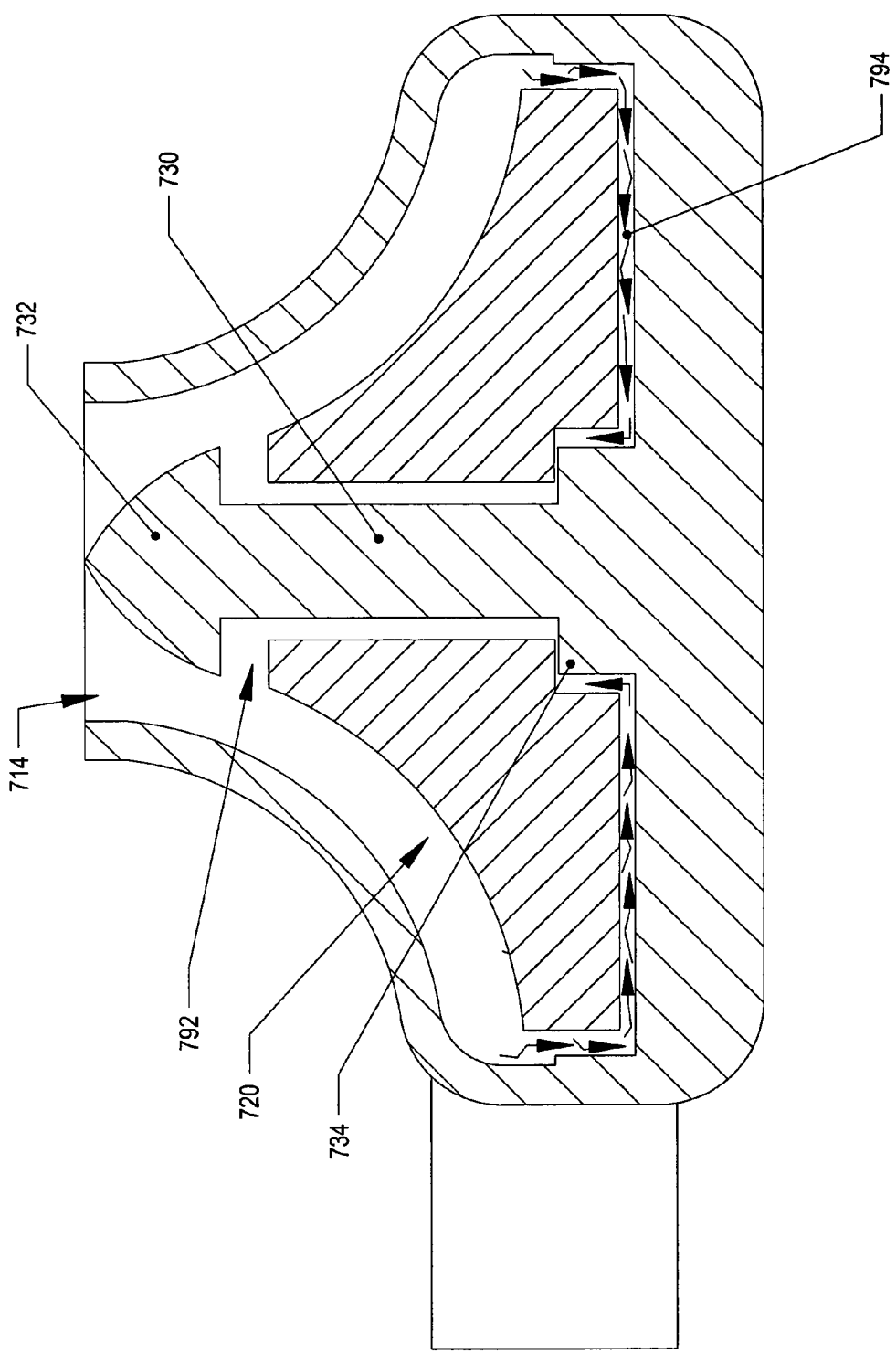
FIG. 7 illustrates an axial hydrostatic bearing in a second position.

Another type of non-contacting bearing is a hydrostatic bearing. FIGS. 6 and 7 illustrate a pump with an axial hydrostatic thrust bearing. The axial hydrostatic bearing may be combined with or used in lieu of the axial magnetic thrust bearings of FIGS. 1-5.

The axial hydrostatic forces are created by the rotor during rotation. Referring to FIGS. 6 and 7, the spindle 630, 730 includes a step 634, 734 that serves to regulate the hydrostatic bearing and the axial position of the rotor.

FIG. 7 illustrates starting conditions for the pump. When the rotor 720 rotates, a pressure differential rapidly develops between the area above the impeller blades and the area 794 between the blades and lower housing. When there is no gap between the step 734 and the rotor, the pressure in area 794 will be greater than the pressure above the blades creating lift for the rotor. As the rotor lifts away from the lower housing, the gap between the step 794 and rotor 720 increases.

Referring to FIG. 6, once the rotor lifts away from the lower housing and the step 634, a pressure relief path becomes available through the bore of the rotor. If the hydrostatic pressure is too great, the rotor will move away from the lower housing toward the pump inlet 614. This increases gap 694. In the illustrated embodiment, the spindle includes a head portion that serves as a rotor stop to prevent the rotor from translating too far along the longitudinal axis of the spindle. The spindle, however, may omit the head portion in an alternative embodiment.

As the rotor moves towards the lower housing, gap 694 decreases. This restricts the pressure relief path through the bore and allows pressure to start building below the blades again. The step (634, 734) serves as a self-regulating throttle for the axial hydrostatic bearing.

The term "step" refers to a transition in cross-sectional area. In one embodiment the cross-section is circular. The size of the gap 694 is a function of the displacement of the rotor from the lower housing and the shape or profile of the step 634 and of the opposing portion 636 of the rotor.

Mathematically, the profile of the step may consist of one or more discontinuities aside from the endpoints defined by the spindle and the housing. Referring to callout 650, the transition between the spindle and the housing may be continuous (650 (b), (c), (d)). Alternatively, the transition may comprise one (e.g., 650 (a)) or more (e.g., 650 (e)) discontinuities. In the illustrated variations, the profile of the step is monotonic. Any curvature of the profile between discontinuities (or between the endpoints) may be concave 650 (b) or convex 650 (c).

The slope of the profile of the step may vary between discontinuities or the endpoints. Profile 650 (d) for example, corresponds to a conical step (i.e., a step formed of a conical frustum). Profile 650 (e) corresponds to a series of stacked conical frustums.

In various embodiments, the profile of the opposing portion 636 of the rotor is substantially complementary to the profile of the step 634. Generally in such cases, there is a rotor axial displacement for which the gap is substantially constant (see, e.g., profiles (a), (b), (c), and (e)). Alternatively, the opposing portion 636 of the rotor need not be precisely complementary to the step 634. Thus there may not be a rotor axial displacement for which the gap between the step 634 and opposing portion 636 of the rotor is constant (see, e.g., profiles 650 (d), (f)). The step and opposing portion of the rotor illustrated in profile (d), for example, are both generally conical but have different slopes. Profile 650 (f) illustrates a curved step working in conjunction with a conical opposing portion of the rotor.

Figure 8:
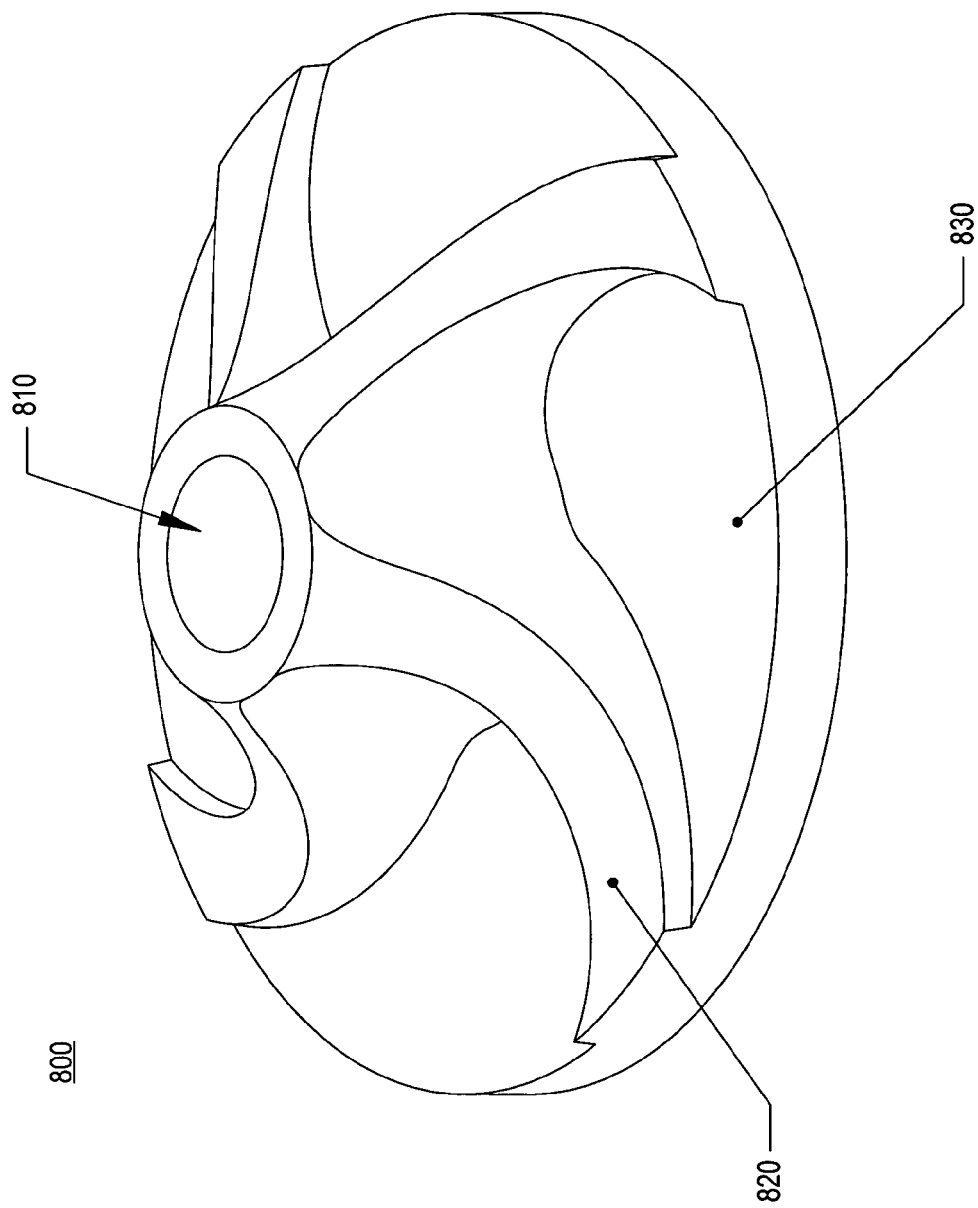
FIG. 8 illustrates one embodiment of an impeller.

FIG. 8 illustrates one embodiment of the rotor 800 including an impeller. The rotor 800 includes a plurality of blades 820 used for pumping the working fluid such as blood. The rotor includes a bore 810. The rotor bore is coaxially aligned with the longitudinal axis of the spindle within the pump housing. Drive magnets (not illustrated) are disposed within the non-bladed portion 830 of the rotor (i.e., within the rotor but not within any blades of the impeller portion of the rotor).

The motor rotor and pump impeller are thus integrated so that a drive shaft is not required. Elimination of the drive shaft also permits elimination of shaft seals for the pump.

Figure 9:
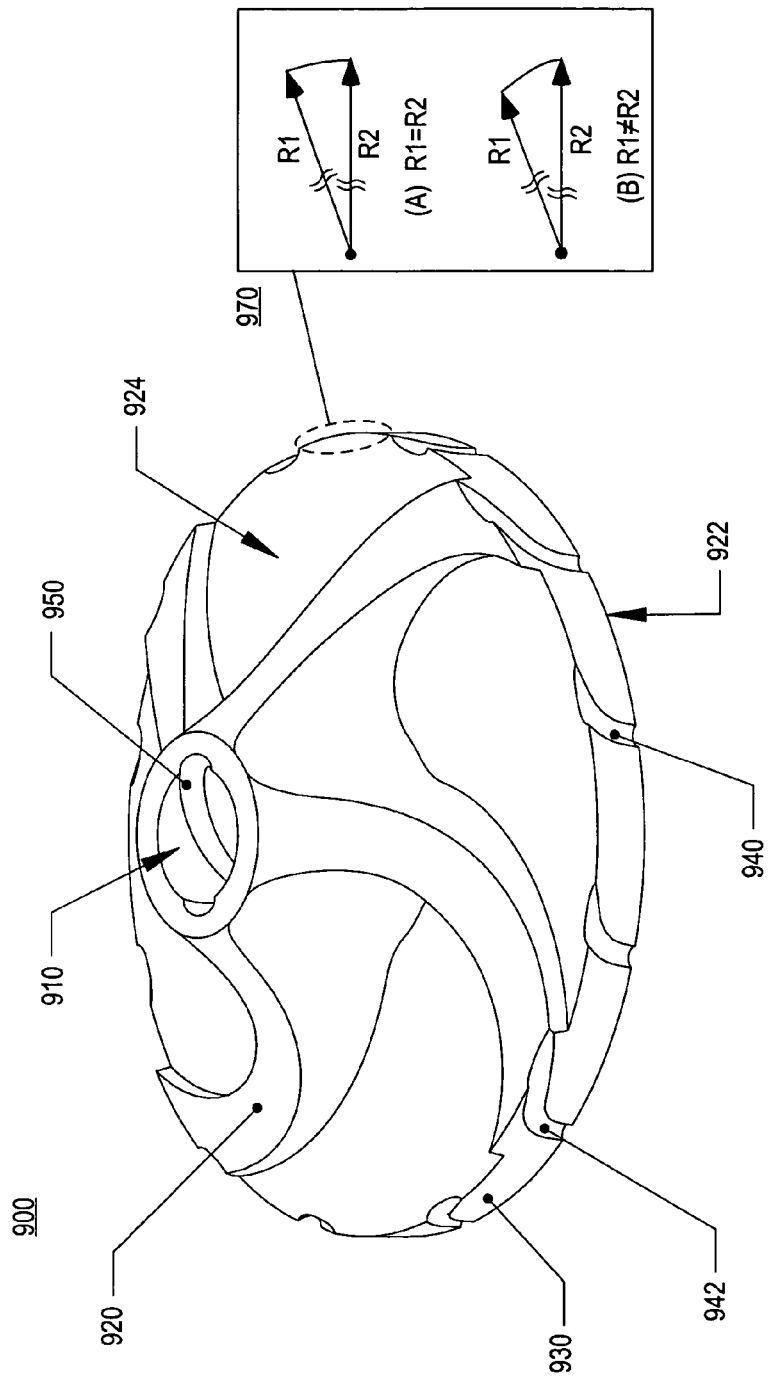
FIG. 9 illustrates an alternative embodiment of an impeller with grooved surfaces for creating a hydrostatic bearing.

FIG. 9 illustrates an alternative embodiment of the rotor. Rotor 900 similarly includes a bore 910 and a plurality of pumping blades 920. The rotor includes additional features to create hydrostatic thrust forces while rotating. In one embodiment, the rotor has a grooved bore. In particular, the bore has one or more helical grooves 950. The bore grooves have a non-zero axial pitch. The groove is in fluid communication with the working fluid of the pump during operation of the pump.

Alternatively or in addition to the grooved bore, the rotor includes a plurality of grooves 940 located at a periphery of the rotor. The peripheral grooves may be located exclusively on the non-bladed portion of the rotor as illustrated in which case the peripheral grooves extend from a lower face 922 to an upper face 924 of the rotor. In an alternative embodiment, the peripheral grooves extend from the lower face 922 to the top of the blades 920 as indicated by groove 942. The peripheral grooves and bore grooves provide hydrostatic thrust during rotation of the rotor. Various embodiments include the bore groove, the peripheral grooves, or both.

Figure 10:
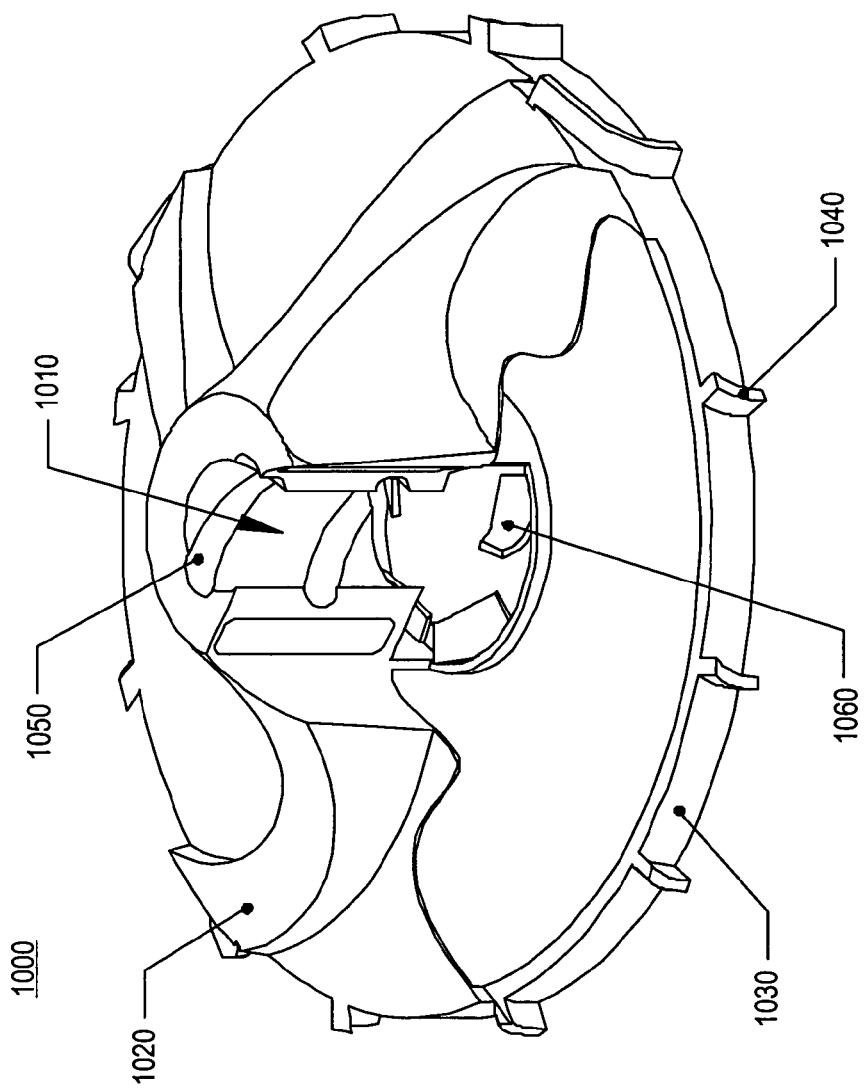
FIG. 10 illustrates an alternative embodiment of an impeller with bladed surfaces for creating a hydrostatic bearing.

FIG. 10 illustrates another embodiment of the rotor. Rotor 1000 includes a bore 1010, a non-bladed portion 1030, and a plurality of pumping blades 1020. The rotor may have grooves 1050 within the bore. The rotor includes paddles 1040 located at the periphery of the rotor. The paddles 1040 are distinct from any pumping blades 1020. The grooved bore and peripheral paddles provide hydrostatic thrust during rotation of the rotor. Various embodiments include the bore groove, the peripheral paddles, or both.

Aside from any magnetic or hydrostatic bearings, the pump may include a hydrodynamic bearing as described with respect to FIGS. 1 and 4. Hydrodynamic bearings rely on the geometry and the relative motion of two surfaces to generate pressure. The rotor or the housing or both may include features to support a hydrodynamic bearing. Various surface geometries suitable for hydrodynamic bearings include grooves and tapers. The groove or taper patterns and location of the grooves or tapers may be chosen to meet specific design constraints. In various embodiments, one of the hydrodynamic surfaces has grooves arranged in a spiral or a spiral herringbone pattern.

Referring to FIG. 9, for example, the rotor may include features at its periphery to generate a radial hydrodynamic bearing. The radius of the periphery of the non-bladed portion of the rotor 930, for example, may vary in size to create a taper between the grooves. Referring to 970 (a), the radial distances (R1, R2) measured from the center of the rotor to two different points along the periphery of the rotor between the grooves is substantially the same such that R1=R2. Referring to 970 (b), the radial distances (R1, R2) measured from the center of the rotor to two different points between the grooves of the rotor are substantially distinct. In one embodiment, R1<R2 to create a tapered outer periphery between the grooves.

Figure 11B:
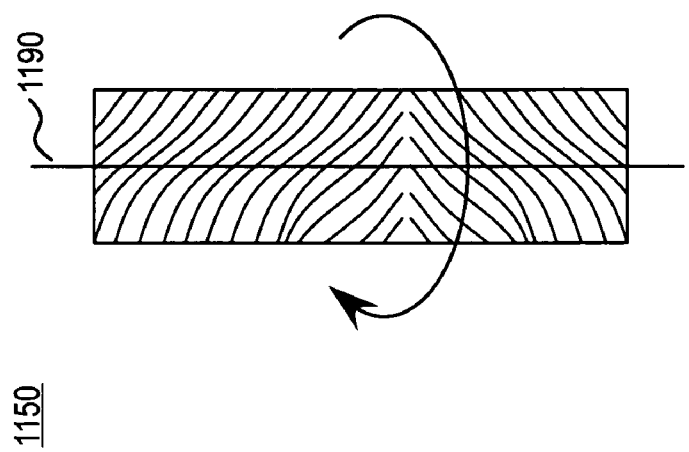
FIGS. 11A and 11B illustrate embodiments of grooved surfaces for creating hydrostatic bearings.
Figure 11A:
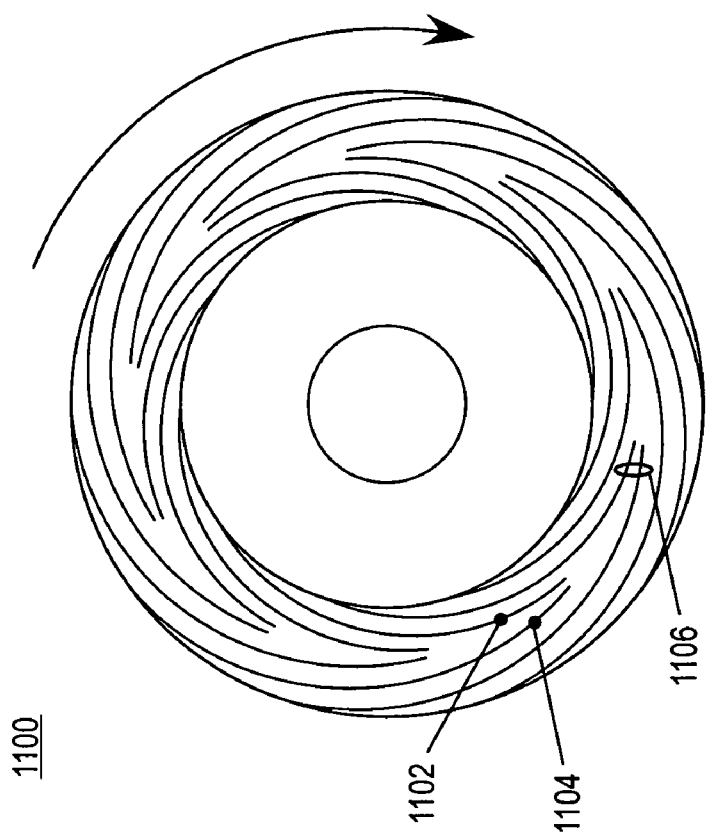

FIGS. 11A and 11B illustrate embodiments of surface geometries suitable for thrust or journal hydrodynamic bearings. The surface geometries comprise groove patterns for axial (thrust) and radial (journal) hydrodynamic bearings. The groove patterns may be located on either the rotor or on an associated portion of the housing (or spindle).

FIG. 11A illustrates a groove pattern for an axial hydrodynamic bearing. Although the groove pattern is illustrated as being disposed on the bottom of rotor 1100 (see, e.g., reference 124 of FIG. 1), the groove pattern may alternatively be located on the lower housing portion that faces the bottom of the rotor (see, e.g., reference 118 of FIG. 1).

Rotor 1100 includes a plurality of nested grooves. Grooves 1102 and 1104, for example, form a curved groove pair that is "nested" within another groove pair 1106. The illustrated groove patterns may also be described as a herringbone or spiraled herringbone pattern. When the rotor rotates in the direction indicated, hydrodynamic thrust forces (i.e., orthogonal to the rotor base) are generated to push the bottom of the rotor away from the facing lower housing portion when the clearance between the bottom of the rotor and the lower housing portion falls below a pre-determined threshold.

FIG. 11B illustrates one embodiment of a rotor bore cross-section 1150 exhibiting a groove pattern suitable for a radial hydrodynamic bearing relative to the rotor axis of rotation 1190. This groove pattern may reside on the rotor bore surface as shown or on the periphery of the rotor. Alternatively, the groove pattern may reside on the spindle or on the wall of the pumping chamber (opposing the periphery of the rotor). As with the example of FIG. 11A, the grooves are nested. This pattern is referred to as a herringbone groove. With respect to FIG. 11A or 11B, the grooves may be chemically, thermally, or mechanically etched into the surface they are disposed upon.

The grooved bore and peripheral grooves or paddles effectively generate auxiliary hydrostatic thrust forces that are applied to the backside of the rotor. These auxiliary hydrostatic axial forces supplement the hydrostatic forces generated by the impeller blades.

In various embodiments, the axial hydrostatic bearing may be combined with a radial hydrodynamic bearing as discussed with respect to FIGS. 1 and 4. Referring to FIG. 9, the grooved bore 910 may support both hydrodynamic journal bearing as well as an axial (thrust) hydrostatic bearing. Preferably, however, the bore is not relied upon for both hydrodynamic journal and thrust bearings. Hydrostatic thrust and hydrodynamic journal bearings may, however, be combined at the periphery of the rotor. Obviously, the rotors of FIGS. 8-9 have greater suitability for the peripheral hydrodynamic bearing than the paddled rotor of FIG. 10.

Figure 12:
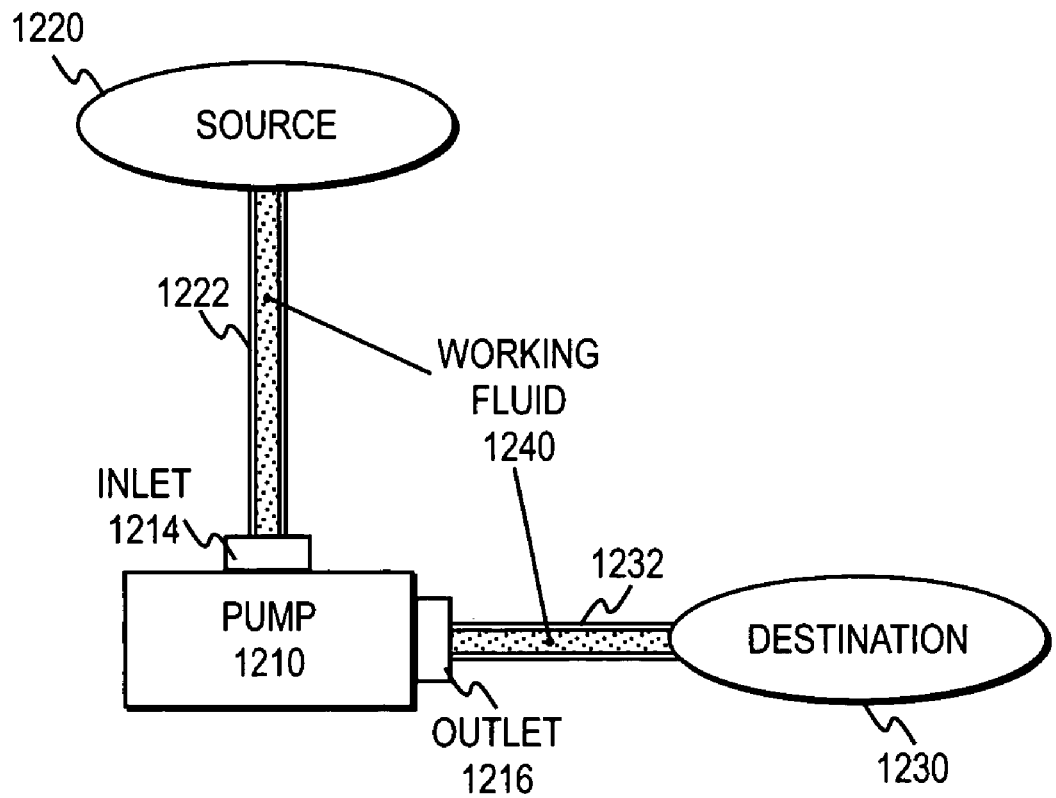
FIG. 12 illustrates one embodiment of the pump used in a medical application.

FIG. 12 illustrates the pump 1210 operationally coupled to move a working fluid 1240 from a source 1220 to a destination 1230. A first working fluid conduit 1222 couples the source to the pump inlet 1214. A second working fluid conduit 1232 couples the pump outlet 1216 to the destination. The working fluid is the fluid moved by the pump from the source to the destination. In a medical application, for example, the working fluid might be blood. In one embodiment, the source and destination are arteries such that the pump moves blood from one artery to another artery.

Various "contactless" bearing mechanisms have been described as alternatives to mechanical contact bearings for rotary pumps. In particular, rotor, impeller, and housing design features are provided to achieve hydrodynamic, hydrostatic, or magnetic bearings. These design features may be used in conjunction with each other, if desired.

In the preceding detailed description, the invention is described with reference to specific exemplary embodiments thereof. Various modifications and changes may be made thereto without departing from the broader spirit and scope of the invention as set forth in the claims. The specification and drawings are, accordingly, to be regarded in an illustrative rather than a restrictive sense.

What is claimed is:

1. A pump apparatus comprising:
   a pump housing defining a pumping chamber, the pump housing having a spindle extending into the pumping chamber; and
   an upper spindle magnet disposed within an upper portion of the spindle; and
   a lower spindle magnet disposed within a lower portion of the spindle,
   wherein the upper and lower spindle magnets are arranged to provide magnetic forces parallel to a longitudinal axis of the spindle.

2. The apparatus of claim 1 wherein at least one of the housing and the spindle has a surface geometry suitable for supporting a hydrodynamic bearing.

3. The apparatus of claim 2 wherein the surface geometry comprises a plurality of spiral grooves.

4. The apparatus of claim 2 wherein the surface geometry comprises a herringbone groove.

5. The apparatus of claim 1 further comprising:
   a rotor configured to rotate about the spindle; an upper rotor magnet carried by the rotor;
   a lower rotor magnet carried by the rotor, wherein the upper spindle and rotor magnets are arranged to repel each other,
   wherein the lower spindle and rotor magnets are arranged to repel each other.

6. The apparatus of claim 5 wherein magnetic vectors of the upper and lower spindle magnets oppose each other.

7. The apparatus of claim 5 wherein magnetic vectors of the upper and lower spindle magnets have a same direction.

8. The apparatus of claim 5 wherein at least one of the rotor, the housing, and the spindle has a surface geometry suitable for supporting a hydrodynamic bearing.

9. The apparatus of claim 8 wherein the surface geometry comprises a plurality of spiral grooves.

10. The apparatus of claim 8 wherein the surface geometry comprises a herringbone groove pattern.

* * * * *